US00PP10250P

United States Patent [19]

Zaiger et al.

[11] Patent Number: Plant 10,250

[45] Date of Patent: Feb. 24, 1998

[54] NECTARINE TREE "HONEY BLAZE"

[76] Inventors: Chris Floyd Zaiger, 929 Grimes Ave.; Leith Marie Gardner, 1207 Grimes Ave.; Gary Neil Zaiger, 1907 Elm Ave.; Grant Gene Zaiger, 4005 California Ave, all of Modesto, Calif. 95358

[21] Appl. No.: 775,032

[22] Filed: Dec. 27, 1996

[51] Int. Cl.[6] ..... A01H 5/00

[52] U.S. Cl. ..... Plt./41.1

[58] Field of Search ..... Plt./41.1

*Primary Examiner*—James R. Feyrer

[57] ABSTRACT

A new and distinct variety of nectarine tree (*Prunus persica* var. *nucipersica*) which has the following unique combination of features that are desirable in a new variety:

1. Fruit with sweet, mild, subacid flavor with excellent eating quality.
2. Regular and productive bearer of large size fruit.
3. Fruit with firm flesh and good handling and shipping quality.
4. Fruit with a high degree of attractive red skin color.
5. Fruit that will stay firm on the tree 12 to15 days after maturity (shipping ripe).
6. Vigorous, upright growth.
7. The ability to produce relatively uniform size fruit throughout the tree.

1 Drawing Sheet

ORIGIN OF THE VARIETY

Our new and distinct variety of nectarine tree was originated by us in our experimental orchard located near Modesto, Calif., as a second generation selection from the cross of two selected seedlings with field identification numbers 36EB86 and 9GC175. The maternal parent (36EB86) originated from a second generation seedling that was selected from a cross between May Grand Nectarine (U.S. Plant Pat. No. 2,794) and a peach of unknown parentage. The paternal parent (9GC175) originated from a second generation seedling of a cross between an open pollinated seedling of Early Sun Grand Nectarine (U.S. Plant Pat. No. 1,420) and Royal Gold Peach (U.S. Plant Pat. No. 2,663). A large number of these second generation seedlings were planted and maintained under close and careful observation by us and one such seedling with especially desirable fruit characteristics as described above, which is the present variety, was selected for asexual reproduction and commercialization.

ASEXUAL REPRODUCTION OF THE VARIETY

Asexual reproduction of the new and distinct variety of nectarine tree was by budding, as performed by us in our experimental orchard located near Modesto, Calif., which shows that all characteristics of the tree and its fruit run true to the original tree and are established and transmitted through succeeding asexual propagations.

SUMMARY OF THE VARIETY

The new and distinct variety of nectarine tree is of large size, vigorous, upright growth; and a productive and regular bearer of large size, yellow flesh, clingstone fruit having a mild, subacid, sweet taste with excellent flavor and eating quality. The fruit is further characterized by being relatively uniform in size throughout the tree, holding firm on the tree 12 to 15 days after maturity (shipping ripe), having firm flesh with good handling and shipping quality and having a high degree of attractive red skin color. In comparison to the Honey Kist Nectarine (U.S. Plant Pat. No. 9,333), which it closely resembles, the new variety is approximately 7 days earlier in maturity.

PHOTOGRAPH OF THE VARIETY

The accompanying color photographic illustration shows typical specimens of the foliage and fruit of the present new nectarine variety. The illustration shows the upper and lower surface of the leaves, an exterior and sectional view of a fruit divided in its suture plane to show flesh color, pit cavity and the stone remaining in place. The photographic illustration was taken shortly after being picked (shipping ripe) and the colors are as nearly true as is reasonably possible in a color representation of this type.

DESCRIPTION OF THE VARIETY

The following is a detailed botanical description of the new variety of nectarine tree, its flowers, foliage and fruit, as based on observations of specimens grown near Modesto, Calif., with color terminology (except those in common terms) in accordance with Reinhold Color Atlas by A. Kornerup and J. J. Wanscher.

Tree:

*Size.*—Large.
*Vigor.*—Vigorous.
*Form.*—Usually pruned to vase shape.
*Productivity.*—Productive.
*Bearer.*—Regular.
*Density.*—Medium.
*Growth.*—Upright.

Trunk:

*Size.*—Large.
*Texture.*—Medium shaggy.
*Color.*—Brown to grayish brown (5-E-3) to (5-F-8).

Branches:

*Size.*—Medium.
*Texture.*—Smooth to medium rough, varies with age of growth.
*Lenticels.*—Medium number. Medium size.
*Color.*—Light brown to brown (5-D-4) to (5-E-6).

Leaves:

*Size.*—Large. Average length 6⅛". Average width 1⅜".
*Form.*—Lanceolate, pointed.
*Margin.*—Crenate.
*Thickness.*—Medium.
*Surface.*—Smooth.

*Petiole.*—Medium length. Medium thickness.

*Glands.*—Reniform. Medium to large size. Number varies from 1 to 4. Average number 2. Located on lower portion of leaf blade and upper portion of petiole.

*Color.*—Upper surface — green to deep green (28-F-6) to (28-F-7). Lower surface — light green to graylish green (28-E-4) to (28-E-6).

Flower bud:

*Size.*—Large.

*Length.*—Medium.

*Form.*—Plump.

Flowers:

*Size.*—Large, showy.

*Pollen.*—Present, self fertile.

*Blooming period.*—Date of first bloom: Mar. 5, 1996. Date of full bloom: Mar. 11, 1996. Varies slightly with climatic conditions.

*Color.*—Pink.

Fruit:

*Maturity when described.*—Firm ripe.

*Date of first picking.*—Jun. 10, 1996.

*Date of last picking.*—Jun. 15, 1996. Varies slightly with climatic conditions.

*Size.*—Large. Average diameter axially 2¾". Average transversely in suture plane 2½".

*Form.*—Nearly globose, slightly elongated.

*Suture.*—Shallow, extends from base to apex.

*Ventral surface.*—Nearly rounded.

*Apex.*—Varies from very slight apical point to slightly retuse.

*Base.*—Retuse.

*Cavity.*—Rounded to slightly elongated in suture plane. Average depth ½". Average breadth ⅞".

Flesh:

*Ripens.*—Evenly.

*Texture.*—Firm, meaty.

*Fibers.*—Small, tender.

*Aroma.*—Slight to moderate.

*Amygdalin.*—Undetected.

*Eating quality.*—Excellent, mild, sweet, subacid.

*Flavor.*—Excellent.

*Color.*—Varies from yellow to golden yellow (5-A-4) to (5-A-5). Pit cavity varies from grayish yellow to brownish yellow (5-B-4) to (5-B-5). Some slight bleeding of red (9-C-8) from pit cavity, primarily toward apex.

Skin:

*Thickness.*—Medium.

*Texture.*—Medium, tough, tenacious to flesh.

*Down.*—Wanting.

*Tendency to Crack.*—None.

*Color.*—Yellow to golden yellow ground color (5-A-4) to (5-A-5). Overspread with red to cardinal red (10E-8) to (10-D-8). Small areas of yellow ground color surfacing through gives a slight mottling pattern in some areas.

Stone:

*Type.*—Clingstone.

*Size.*—Large. Average length 1½". Average width 1⅛". Average thickness ¾".

*Surface.*—Furrowed toward apex, pitted throughout, heavier toward the base, pits vary from round to elongated.

*Base.*—Rounded.

*Apex.*—Acuminate.

*Form.*—Varies from ovoid to obovoid.

*Sides.*—Usually unequal, varies from equal to unequal.

*Tendency to split.*—None.

*Color.*—Light brown to brown (7-C-5) to (7-D-5).

Use: Dessert. Market, local and long distance.

Keeping quality: Good.

Shipping quality: Good.

The present new variety of nectarine tree, its flowers, foliage and fruit herein described may vary in slight detail due to climate, soil conditions and cultural practices under which the variety may be grown. The present description is that of the variety grown under the ecological conditions prevailing near Modesto, Calif.

We claim:

1. A new and distinct variety of nectarine tree, substantially as illustrated and described, characterized by its large size, vigorous, upright growth and being a productive and regular bearer of large size, firm, yellow flesh, clingstone fruit having a mild, sweet, subacid taste with excellent flavor and eating quality, and maturing approximately 7 days earlier than Honey Kist Nectarine (U.S. Plant Pat. No. 9,333); the fruit days after maturity, (shipping ripe), having good handling and shipping quality and being relatively uniform in size throughout the tree.

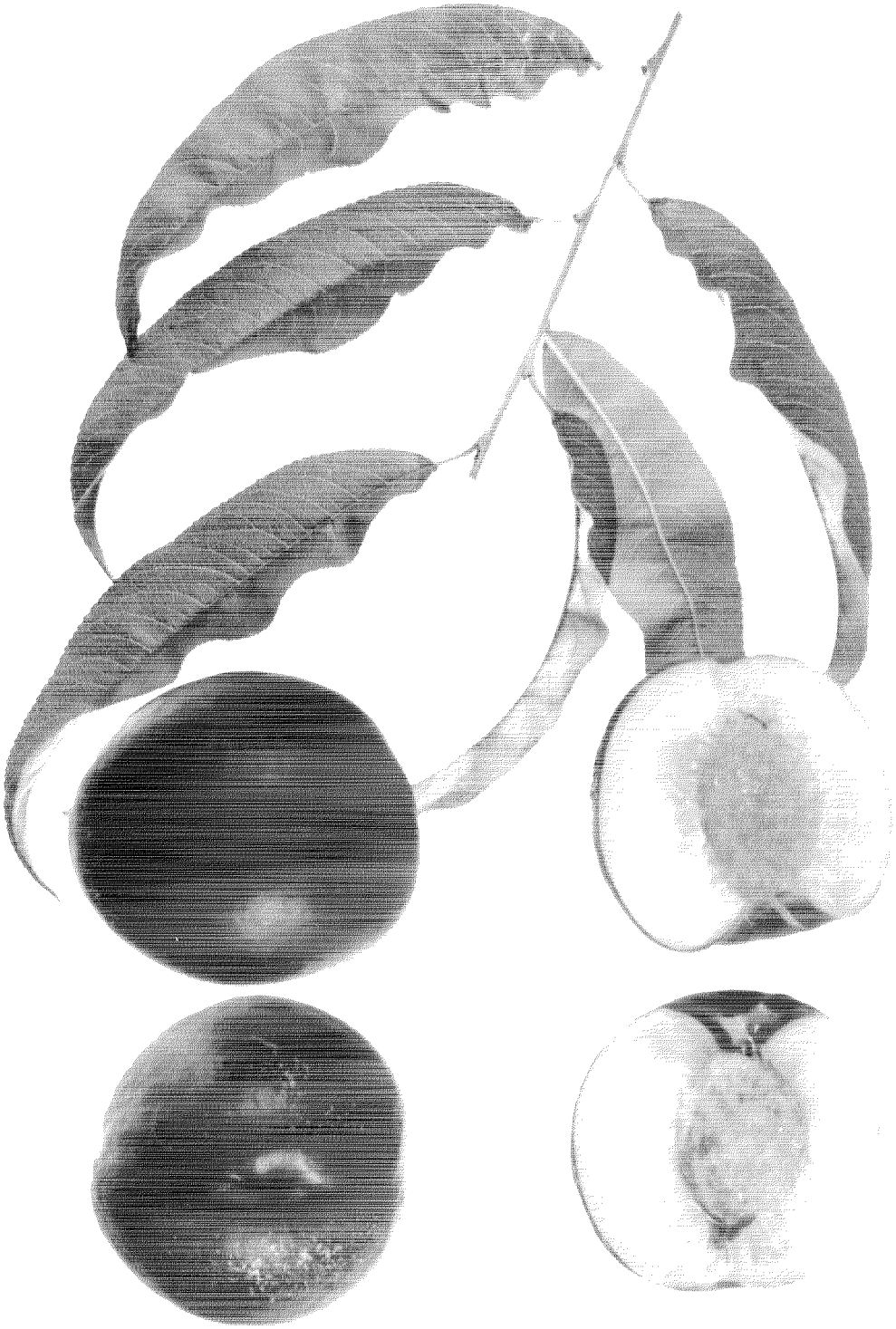

* * * * *